US010625010B2

(12) United States Patent
Iske et al.

(10) Patent No.: US 10,625,010 B2
(45) Date of Patent: Apr. 21, 2020

(54) BLOOD TREATMENT DEVICE WITH SEPARATE DOOR COMPARTMENT

(71) Applicant: B. BRAUN AVITUM AG, Melsungen (DE)

(72) Inventors: Andreas Iske, Soehrewald (DE); Bruno Stenzel, Hann. Muenden (DE)

(73) Assignee: B. Braun Avitum AG (DE)

(*) Notice: Subject to any disclaimer, the term of this patent is extended or adjusted under 35 U.S.C. 154(b) by 10 days.

(21) Appl. No.: 15/066,449

(22) Filed: Mar. 10, 2016

(65) Prior Publication Data

US 2016/0271310 A1  Sep. 22, 2016

(30) Foreign Application Priority Data

Mar. 17, 2015 (DE) .................. 10 2015 103 937

(51) Int. Cl.
*A61M 1/14* (2006.01)
*A61M 1/16* (2006.01)
*A61B 5/022* (2006.01)

(52) U.S. Cl.
CPC .......... *A61M 1/1668* (2014.02); *A61B 5/022* (2013.01); *A61M 1/14* (2013.01); *A61M 1/1621* (2014.02); *A61M 2205/15* (2013.01); *A61M 2205/75* (2013.01); *A61M 2209/08* (2013.01)

(58) Field of Classification Search
CPC .... A61M 1/1668; A61M 1/14; A61M 1/1621; A61M 2205/15; A61M 2205/17; A61M 2209/08; A61B 5/022; A47B 45/00
See application file for complete search history.

(56) References Cited

U.S. PATENT DOCUMENTS

| 7,420,660 | B2 | 9/2008 | Muller |
| 8,940,233 | B2 | 1/2015 | Kang et al. |
| D730,958 | S * | 6/2015 | Choi ............................ D15/91 |
| 2003/0138349 | A1 | 7/2003 | Robinson et al. |
| 2004/0064080 | A1 | 4/2004 | Cruz et al. |
| 2006/0060540 | A1 | 3/2006 | Muller |
| 2006/0243619 | A1* | 11/2006 | Brown ............... A61M 5/3205 206/366 |
| 2009/0105629 | A1 | 4/2009 | Grant et al. |
| 2010/0252490 | A1* | 10/2010 | Fulkerson ........... A61M 1/1656 210/96.2 |

(Continued)

FOREIGN PATENT DOCUMENTS

| CN | 2711858 Y | 7/2005 |
| CN | 1708338 A | 12/2005 |

(Continued)

OTHER PUBLICATIONS

European Search Report for EP 16 160 153.9 dated Jul. 12, 2016, with translation.

(Continued)

*Primary Examiner* — Bobby Ramdhanie
*Assistant Examiner* — Donovan Bui-Huynh
(74) *Attorney, Agent, or Firm* — RatnerPrestia

(57) ABSTRACT

A housing for a dialysis machine, with a wall, an opening which is provided in the wall, and a door by means of which the opening can be closed. The door or an additional wall has an installation space for a device component, which can be closed by means of an additional door.

11 Claims, 3 Drawing Sheets

(56) References Cited

U.S. PATENT DOCUMENTS

| | | | |
|---|---|---|---|
| 2011/0009796 A1* | 1/2011 | Tullis | A61M 1/3486 604/5.02 |
| 2011/0098635 A1 | 4/2011 | Helmore et al. | |
| 2012/0061310 A1 | 3/2012 | Beden et al. | |
| 2012/0181296 A1 | 7/2012 | Syfonios | |
| 2014/0112828 A1* | 4/2014 | Grant | A61M 1/3643 422/44 |
| 2015/0165105 A1 | 6/2015 | Beden et al. | |
| 2015/0241116 A1* | 8/2015 | Choi | E05B 65/0042 312/404 |
| 2016/0271310 A1 | 9/2016 | Iske et al. | |

FOREIGN PATENT DOCUMENTS

| | | | |
|---|---|---|---|
| CN | 101676003 A | | 3/2010 |
| CN | 101842703 A | | 9/2010 |
| CN | 102206273 A | * | 10/2011 |
| CN | 202305529 U | | 7/2012 |
| CN | 205487363 U | | 8/2016 |
| DE | 102 24 750 | | 12/2003 |
| DE | 600 31 947 | | 9/2007 |
| DE | 10 2009 045 095 | | 4/2011 |
| EP | 0 432 146 | | 6/1991 |
| JP | 01502091 A | | 7/1989 |
| JP | 11137673 A | | 5/1999 |
| JP | 2000107287 A | | 4/2000 |
| JP | 2006501000 A | | 1/2006 |
| WO | 198802641 A1 | | 4/1988 |
| WO | 2004028594 A1 | | 4/2004 |
| WO | WO 2008010004 | | 1/2008 |

OTHER PUBLICATIONS

German Search Report for DE 10 2015 103 937.0 dated Oct. 8, 2015, with translation.
Japanese Information Sheet for Japanese Application No. 2016-051583, dated Apr. 10, 2019, 7 paages.
Chinese Office Action for Chinese Application No. 201610149789.6, dated Oct. 28, 2019 with partial translation, 10 pages.
Japanese Notification of Reasons for Refusal for Japanese Application No. 2016-51583, dated Jan. 14, 2020, with translation, 12 pages.

* cited by examiner

BLOOD TREATMENT DEVICE WITH SEPARATE DOOR COMPARTMENT

CROSS REFERENCE TO RELATED APPLICATIONS

This application claims priority to German application DE 10 2015 103 937.0 filed Mar. 17, 2015, the contents of such application being incorporated by reference herein.

FIELD OF THE INVENTION

The invention in hand concerns a blood treatment device with a separate carrier compartment integrated in the door for device components, and in particular a housing for a blood treatment device. A dialysis machine is also to be classified as a blood treatment device of the type according to aspects of the invention.

BACKGROUND OF THE INVENTION

As far as a blood treatment device, in particular a dialysis machine, is concerned, the safety of the operator and/or the patient is important, among others. For example, when the dialysis machine is operated in the disinfection mode, the dialysis fluid filters get very hot in particular, and because the dialysis fluid filters are usually attached on the outside of a housing of the dialysis machine, there is an increased risk of injury for the operator and/or the patient. Furthermore, dialysis fluid filters attached on the outside present, in addition to an increased space requirement, the risk that hose connections are accidentally detached from the dialysis fluid filters during handling of the device and that this causes a leak. For example, when the dialysis machine is moved to a different location, the dialysis fluid filters attached on the outside may also get damaged. In addition, it is not possible or only possible with a lot of effort to detect a leak on dialysis fluid filters attached on the outside, and consequently an ultra-filtration deviation that puts the patient at risk would remain undetected.

In that connection, a simple placement of the dialysis fluid filters in the housing of the dialysis machine is no workable solution because the dialysis fluid filters need to be easily accessible, for example during operation and maintenance. In addition, dialysis fluid filters moved inside the housing would reduce the space available there and impair the accessibility of other components placed in there.

DESCRIPTION OF THE RELATED ART

A housing for a blood treatment device with cover flap is known from DE 10 2009 04 50 95 A1. On this housing, an opening can be closed by means of a cover flap on the inside of which an extracorporeal blood treatment module is provided. There, a coupling element is mounted pivotable towards a housing wall around a first axis of rotation, and the cover flap is mounted pivotable towards the coupling element around a second axis of rotation. The goal of this is that the extracorporeal blood treatment module is accessible and that the displays and control elements for the extracorporeal blood treatment module that are installed on the outside of the cover flap are visible and accessible, respectively, when the cover flap is in the folded-out position.

The disadvantage of this is that even if only access to other components inside the housing is necessary, the cover flap has to be opened and consequently the extracorporeal blood treatment module also has to be pivoted outwards at least partly even if no work is to be performed on it at all. That makes unintended alterations on the extracorporeal blood treatment module, in particular on connections affixed to it, possible in the first place. In addition, the extracorporeal blood treatment module prevents free access to other components installed inside the housing in that way.

SUMMARY OF THE INVENTION

In the face of this known state of the art, the basic task of the invention is to describe a blood treatment device, preferably a dialysis machine, which allows for an improved protection of a device component to be installed inside of it or to be affixed to it with easy accessibility of the same.

A device component in the sense of the invention refers to a component to be arranged in or on the housing of the blood treatment device according to aspects of the invention and initially also includes device accessories. Preferably, the term device components refers to the parts of the blood treatment device which are usually arranged on the outside of the housing for reasons of simplified handling, such as dialysis filters, device-side supply and discharge hosepipes, cartridges that contain additives for the preparation of the dialysis fluid, etc.

Another objective of the invention is to make available a blood treatment device, preferably a dialysis machine, with a housing where a device component of the blood treatment device normally arranged outside the housing is protected from unintentional alteration, in particular from damage, and is still easily accessible.

Finally, an objective of the invention is not to impair the accessibility of those device components which are, as is known, arranged inside the device even when the device concept in hand is implemented.

The objectives are achieved by means of a blood treatment device, preferably a dialysis machine, with the characteristics according to the independent claim. Preferred embodiments of the invention in hand are subject of the respective sub-claims.

The invention relates to the general concept of integrating those device components, in particular dialysis filters, which used to be arranged outside the device housing according to the state of the art, into the housing as well. However, they are to be placed in the housing in such a way that the volume inside the device housing is not unduly limited and that access to the device components usually arranged inside the device housing, such as pumps, heat exchangers, sensors, etc., is not impaired. This idea can be conceptually realized by integrating the device components that are normally arranged outside the device housing in a housing compartment separate from the device housing, but preferably at least partially inside the device housing, which compartment can be spaced apart/placed at a distance from the device housing in order to create access space for the device components that remain in there.

In principle, the invention in hand capitalises on the structural concept of, for example, a generally known refrigerator as it can be found in conventional kitchens. There, separate storage compartments are realized for fragile foodstuffs or containers, for example on the inside of the refrigerator door, which are separated from the remaining interior of the refrigerator with an inside door or flap and which are pivoted away along with the refrigerator door from the inside of the refrigerator in order to improve access to the inside of the refrigerator.

Based on this structural concept, the invention provides a door-in-door design where a housing door (that is present anyway) is realized for releasing/closing a device housing access with a hollow space/carrier compartment which can be closed with a further compartment door or flap (outside door or inside door), which is again fastened and/or attached with hinges on the housing door, preferably on its outside, in order to achieve the set objective. This means that the device housing door serves as a carrier compartment for the device components that are normally arranged outside the device housing, preferably filters/filter cartridges, at the same time so that these are inevitably pivoted away/displaced with the device housing door from the blood treatment device/dialysis machine when an access is to be opened up to the inside of the housing.

Despite this separate integration in the device housing door, the access to the inside of the housing as well as the access to the device components integrated in the housing door consequently remain almost unobstructed. In that way, the device components normally arranged outside the device housing can be replaced, for example, with only a minor extra effort, namely the opening (from the outside) of the compartment door or flap (with the device housing door opened as well as closed). However, they sit there protected and the inside of the device door housing is not constrained excessively. Furthermore, the hollow space/compartment designed in the device housing door can extend at least partly or completely in the inside of the housing so that the outside dimensions of the blood treatment device, preferably the dialysis machine, do not have to be enlarged considerably as compared to known devices. As the hollow space/compartment is swivelled along with the device housing door when it is opened, access to the inside of the housing remains unobstructed.

More specifically, a housing according to aspects of the invention of a blood treatment device, preferably a dialysis machine, has at least one wall and one opening that is provided in the wall. Furthermore, the housing has at least one housing door, preferably a service or supply door, with which the opening can be closed. According to aspects of the invention, the door, or an additional wall, has an installation space/compartment for a device component which can be closed with an additional door (door-in-door) preferably fixed on the outside of the housing door.

An advantage of the device housing according to aspects of the invention is that the device component(s) arranged in the separate installation space/door compartment, in particular of the dialysis machine, is/are protected from damage. Another advantage is that an operator and/or a patient is protected from injuries caused by a device component arranged in the installation space/compartment. There, the at least one device component arranged in the installation space/compartment is still easily accessible for further operation and/or maintenance/replacement. In addition, the device housing according to aspects of the invention requires less space because the device component(s) arranged in the installation space/compartment require(s) hardly any space outside the housing.

Further embodiments of the device door specified below shall analogously also apply to the additional wall.

In an advantageous manner, the installation space/compartment is open to the outside and can be closed from the outside with the additional door (compartment door). This improves accessibility of the device component arranged in there even with the device housing door closed.

The installation space/compartment can be realized as a recess, in particular a pan. Furthermore, the installation space/compartment can be separated from the remaining housing interior at least in sections with a grid-like wall.

In an advantageous manner, the device housing door and the additional door can each be operated independently from each other from the outside. In the event that the device housing door (hereinafter also referred to as housing door for the sake of simplicity) is or has to be opened, for example for maintenance of another device component integrated in the housing, the additional door can remain closed and so its multiple protective function for the device component arranged in front of and in the installation space/compartment, respectively, remains intact. In addition, the additional door can be opened for the operation and/or maintenance of the device component arranged in the installation space/compartment without having to open the device door. On the one hand, this improves the accessibility of the device component arranged in the installation space/compartment and, on the other hand, this continues to protect the other device component(s) integrated in front of and in the device housing, respectively.

In an advantageous manner, the additional door is arranged on the device door, in particular on the outside. As a result, the additional door can easily be accessed and operated at any time, not matter whether the device door is open or closed.

In an advantageous manner, the device door and/or the additional door is/are realized as a swing door opening to the outside. As a result, the installation space/compartment arranged on the device door swings, along with the additional door realized as a swing door opening to the outside, out of the device housing and so improves the accessibility of other device components integrated in the device housing, in particular of the dialysis machine. The fact that the additional door is realized alone or also as a swing door opening to the outside furthermore ensures the above-mentioned advantage of improved accessibility of the installation space/department and the device component(s) to be integrated in it and of the device door and additional door that can be opened independently of each other.

Furthermore, it is advantageous to realize the device door and/or the additional door as a sliding door, in particular a multi-part/multi-section one. Depending on the space available in the housing or the housing environs, this design offers further advantages as the device door and the additional door can be opened independently of each other and this ensures an improved accessibility of the installation space/compartment and the device component to be integrated in there, respectively.

In an advantageous manner, a sensor, in particular a position sensor, is provided, with which an open and/or closed position of the device door and/or the additional door can be detected. As a result, an unintentional opening of the additional door can be avoided in particular and the above-mentioned multiple safety function of the additional door remains intact. In addition, an unintentional opening of the device door can be avoided in that way and the other device components remain protected by the housing according to aspects of the invention.

It is also conceivable to prevent, for example, an opening of the device door when the additional door is open with the arrangement of the sensor.

In an advantageous manner, the installation space/compartment is arranged in a way so that it protrudes from the device door to the inside. In that way, device components that require more space can be arranged in the installation space/compartment.

As an alternative or in addition to that, the installation space/compartment may be arranged so that it projects from the device door to the outside. As a result, device components that require more space can be arranged in the installation space/compartment.

In another advantageous manner, the installation space/compartment is arranged/realized roughly flush with the device door on the outside, which results in a reduced outside circumference of the housing according to aspects of the invention.

Furthermore, the installation space/compartment can be arranged roughly flush with the device door on the inside and on the outside. This design of the installation space/compartment that is space-saving to the inside and the outside is advantageous for device components that require less space.

In an advantageous manner, the additional door is arranged in its closed position roughly flush with the device door on the outside. Furthermore, this arrangement enables a small outer frame size of the housing according to aspects of the invention.

In an advantageous manner, the device door is realized as a profile, in particular a multi-part profile, which enables cost-efficient manufacturing. In particular, the installation space/compartment is realized in one piece with the device door, which offers a further advantage with regard to a cost-efficient manufacturing of the device door. Depending on the requirement regarding, for example, manufacturing, storage and/or handling, the installation space/compartment can be realized separately from the device door and affixed to it as required.

In an advantageous manner, the device door can be made of sheet metal or plastic. These materials have been tested in clinical applications and there are hassle-free manufacturing processes for them.

In an advantageous manner, a collection device for the collection of a leakage volume, in particular a dialysis fluid, is provided in the installation space/compartment or in the device door. In that way, a leakage volume that may be produced can be contained and collected in a targeted manner.

In an advantageous manner, a leakage sensor for the registration of the leakage volume is provided. The leakage volume can be safely detected with the collection device in particular in that way. In the case of a dialysis machine as the blood treatment device in particular, an ultra-filtration deviation that puts the patient at risk can be safely detected and the measures necessary in that case can be taken immediately.

In an advantageous manner, the collection device has a bottom area or drip pan which confines the installation space/compartment at least in sections. This guarantees furthermore that a leakage occurring in the installation space/compartment is safely contained and does not contaminate the inside of the housing according to aspects of the invention.

In an advantageous manner, the wall is a rear wall. In the case of a dialysis machine as the blood treatment device in particular, an operation not doing harm to the patient is possible. As an alternative or in addition to that, the wall can also be a side wall or a front wall.

In a blood treatment device, preferably a dialysis machine, with a housing according to aspects of the invention, a device component of the dialysis machine is arranged in the separate installation space/compartment, and this component has a dialysis fluid filter, a bicarbonate cartridge and/or a blood pressure cuff.

In an advantageous manner, the installation space/department has a retainer and/or an interface for the device component(s) contained in the installation space. In particular in the case that the device component has a dialysis fluid filter, the interface contains, for example, a hosepipe duct or a hosepipe connection from and to the inside of the housing, respectively.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
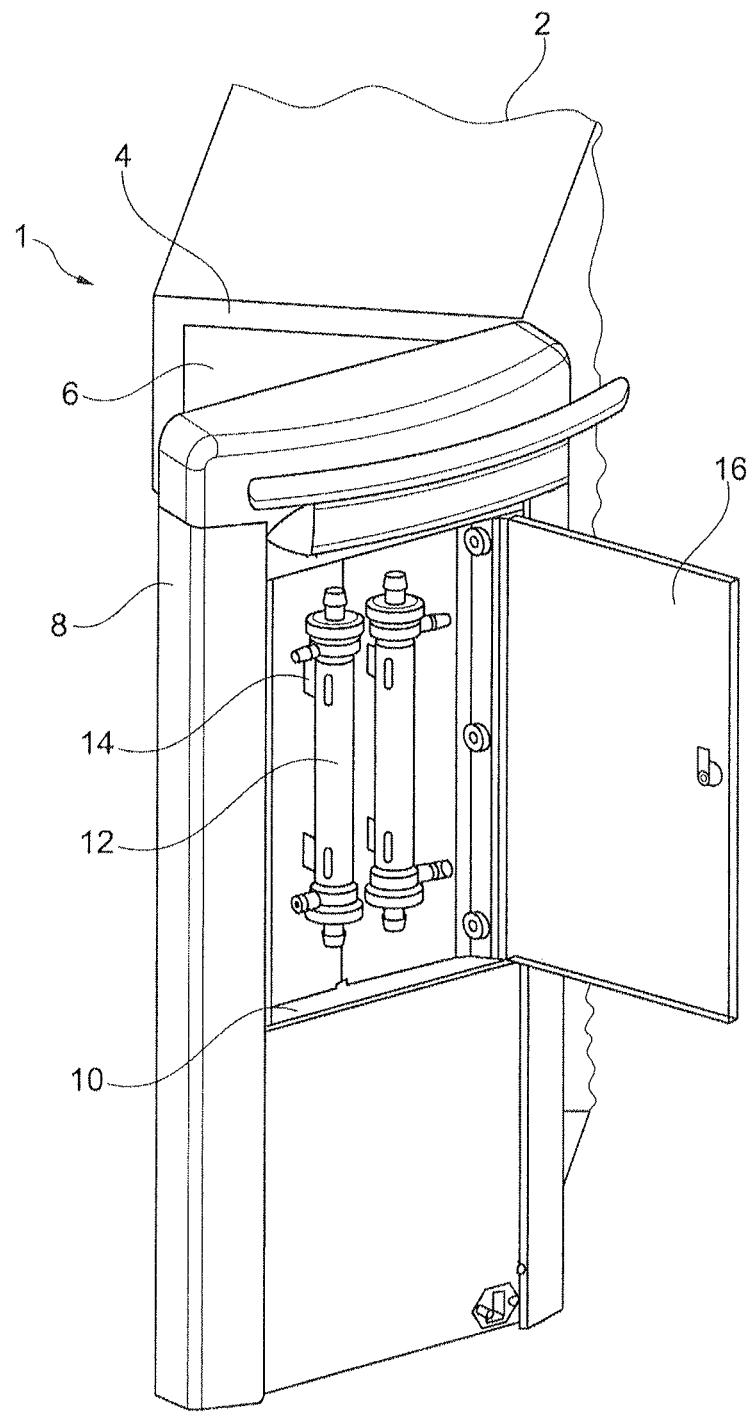
FIG. 1 shows an embodiment of a blood treatment device according to aspects of the invention, preferably a dialysis machine, with a device housing according to aspects of the invention in hand with open device housing door and open additional door in the device housing door.

FIG. 1 shows an exemplary embodiment of the blood treatment device according to aspects of the invention, preferably a dialysis machine 1 with a housing 2 according to aspects of the invention in hand. In one wall 4 of the housing 2, an opening 6 is provided, and on the wall 4, a housing door 8 realized as a swing door is fastened on the side, with which the opening 6 of the housing 2 can be closed, whereby the wall 4 is preferably a rear wall of the housing 2. The housing door 8 contains/forms an installation space/compartment 10 inside the door, which houses one or several device components, dialysis fluid filters 12 here, which are fixed in a detachable manner with a retainer 14 integrated in the compartment and fixed on the device door 8 in each case. The installation space/compartment 10 is realized as a pan open to the outside in the housing door 8, which can be closed (from the outside) with an additional door (16) realized as a swing door laterally fastened to the housing door 8. The installation space 10 has one or several interfaces (accesses) (not shown) such as a hosepipe duct or a hosepipe connection from the inside of the housing 2 for the dialysis fluid filters 12. Via the opening 6, other device components integrated in the housing 2 can be accessed, for example for maintenance purposes. Here, the opening 6 extends across almost the complete (rear) wall 4 in order to ensure the best possible accessibility of the other device components integrated in the housing 2. In an embodiment that is not shown, the opening 6 can constitute a part of the wall 4, depending on the required accessibility of the other device components integrated in the housing 2 and/or depending on the desired stability of the housing 2. However, other common measures, such as a reinforcement of the (side) walls adjacent to the wall 4, can also be taken for stability.

In another embodiment that is not shown, the housing door 8 and/or the additional door 16 affixed to it can be realized as a multi-part sliding door, in particular as a roller blind. Depending on requirement and required space on and around the dialysis machine 1 according to aspects of the invention, the housing door 8 can, for example as shown, be realized as a swing door attached on the right, and the additional door 16 can be provided as a roller blind opening to the bottom (not shown), which runs outside on the housing door 8 or inside in the housing door 8.

The housing door 8 and the additional door 16 can be operated independently of each other in each case from the outside so that, for example in case of necessary maintenance of other device components integrated in housing 2, only the housing door 8 has to be opened and the additional door 16 can remain closed, whereby the dialysis fluid filters 12 arranged in the installation space/compartment 10 continue to be protected from external influences (even when housing door 8 is opened). This also facilitates an operation and/or the maintenance of the dialysis fluid filters 12 arranged in the installation space/compartment 10 because only the additional door 16 has to be opened for that purpose and the housing door 8 can remain closed, whereby the dialysis fluid filters 12 remain easily accessible and the other device components integrated in the housing 2 remain protected, in particular from external influences.

Figure 2:
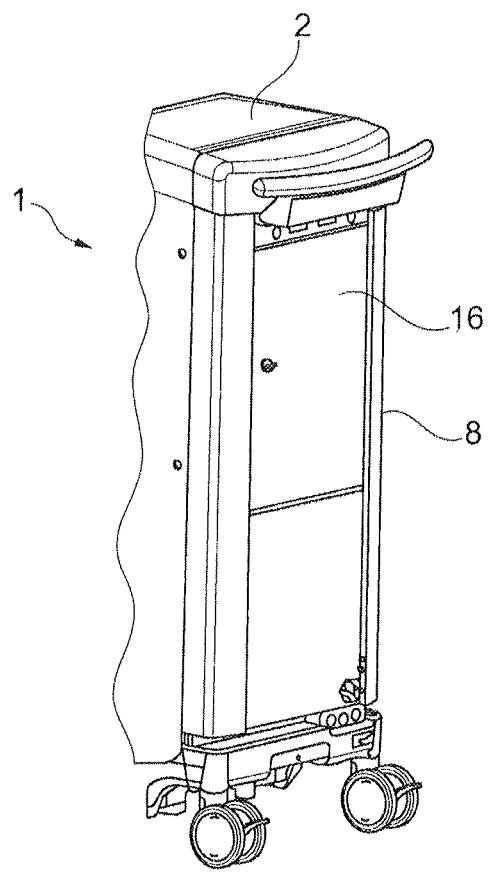
FIG. 2 shows the embodiment of the dialysis machine according to FIG. 1 with closed device housing door and closed additional door.

FIG. 2 shows the embodiment of the blood treatment device, preferably a dialysis machine 1 according to FIG. 1 with closed housing door 8 and closed additional door 16, whereby the additional door 16 is arranged, in its closed position, roughly flush with the housing door 8 on the outside.

Figure 3:
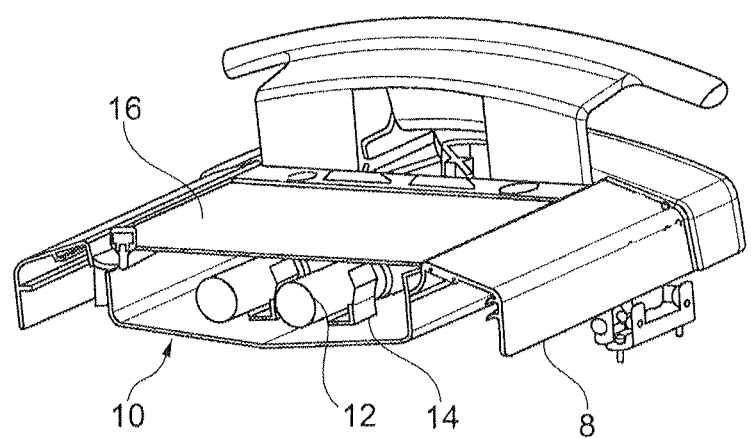
FIG. 3 shows a sliced view of the housing door of the dialysis machine according to FIG. 1 from below at an angle.

As shown in FIG. 3, the housing door 8 is manufactured as a profile in a cost-efficient manner, to which the separately manufactured installation space/compartment 10 is attached as an additional compartment (optionally) on the inside or the outside. In another embodiment that is not shown, the installation space/compartment 10 can be made from one piece together with the housing door 8. The housing door 8 and/or the installation space/compartment 10 can be made of sheet steel or plastic. The installation space 10 is arranged roughly flush with the housing door 8 and its door frame, respectively, on the inside and/or the outside.

Figure 4:
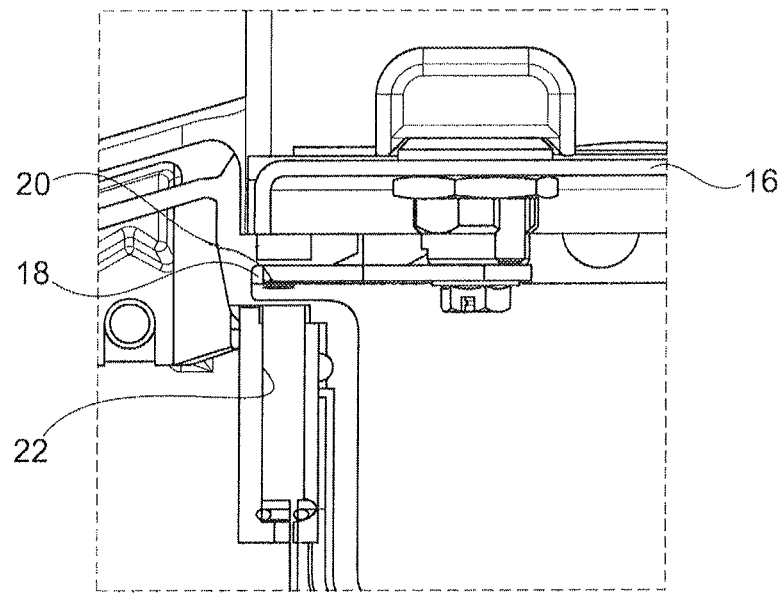
FIG. 4 shows a sliced bottom view of a detail of the housing door of the dialysis machine according to FIG. 1.

The sectional view in FIG. 4 shows how a closed position of the additional door 16 can be detected based on the position of a bolt 18 of the additional door 16 with a magnet 20 which is affixed to the bolt 18 and a sensor 22 that is realized as a position sensor. In the closed position of the additional door 16, the magnet 20 switches the sensor 22. As soon as the magnet 20 is removed from the sensor 22 in order to open the additional door 16, the sensor 22 detects the change and reports an opened additional door 16 to the system. The sensor signal can be passed on to a visual and/or acoustic warning device for the output of a visual and/or acoustic warning.

Here it is to be pointed out that the description above of the sensor recognition of the closed position of the additional door 16 presents only an example and that it can also be carried out in other ways, for example with a mechanically operable position button/switch or the like.

Figure 5:
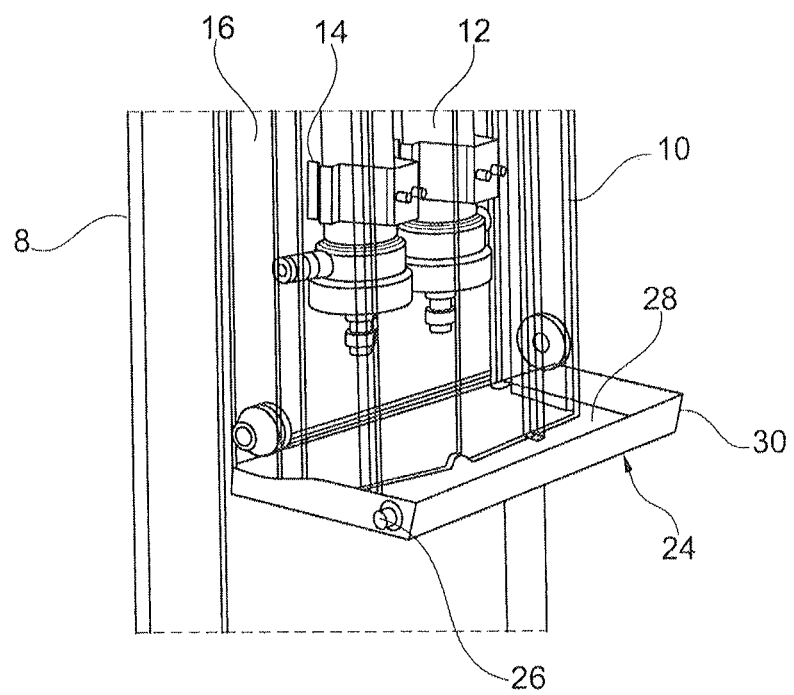
FIG. 5 shows a view of the installation space/compartment of the dialysis machine according to FIG. 1 from the inside at an angle with the walls of the installation space/compartment shown transparent.

FIG. 5 shows a view from the inside at an angle with the walls of the installation space/compartment 10 shown transparent. Here, in the installation space 10, a collection device/drip pan 24 for collecting a leakage volume of a dialysis fluid, in particular from the dialysis fluid filters 12 and/or hosepipes affixed to them, is provided. The collection device 24 that is shaped like a trough has a bottom surface 28 which confines the installation space 10 to the bottom. Furthermore, the collection device 24 has an all-round wall or trough rim 30, the height of which is dimensioned for the leakage volume to be expected.

The leakage volume can be registered with a leakage sensor 26 arranged on the collection device 24, on the wall 30 here. The sensor signal can be passed on to a visual and/or acoustic warning device for the output of a visual and/or acoustic warning.

Disclosed is a housing for a blood treatment device such as a dialysis machine on which an installation space/compartment for a device component is provided on the one (housing) wall, which space is in particular open to the outside, kept separate from the inside of the housing. The installation space can be closed individually with an additional door, whereby the additional door is arranged on the wall. In the case that the wall has an opening, the wall comprises a housing door with which the opening can be closed, whereby the additional door is arranged/fixed with a hinge to the housing door. In a blood treatment device according to aspects of the invention, such as a dialysis machine with the housing according to aspects of the invention in hand, the additional door can be operated independently of the housing door and consequently a device component contained in the installation space/compartment is protected from influences from the outside with the additional door, but it is still easily accessible for purposes of maintenance and/or operation.

The invention claimed is:

1. A dialysis machine comprising:
   a housing having an interior, at least one wall of the housing having an opening for access to the interior of the housing; and
   a housing door coupled to the housing, the housing door configured to cover the opening in a closed position and provide access to the opening in an open position,
   the housing door comprising a front waft, a rear wall offset from the front wall, and an installation space defined between the front wall and rear wall,
   an installation door coupled to the front wall of the housing door, the installation door configured to provide access to the installation space through the front wall,
   the front wall, installation door and rear wall forming a hollow enclosure that encloses the installation space within the housing door,
   the installation space being walled off from the interior of the housing by the rear wall when the housing door is in the closed position,
   the installation space being inaccessible through the rear wall when the housing door is in the open position,
   the installation space configured to hold at least one device component separate from the interior of the housing, wherein in the installation s ace the at least one device component of the dialysis machine is a dialysis fluid filter, and
   the installation door and the housing door being independently operable from outside the housing.

2. The dialysis machine according to claim 1, wherein at least one of the housing door or the installation door is a swing door opening to the outside.

3. The dialysis machine according to claim 1, wherein at least one of the housing door or the installation door is a sliding door.

4. The dialysis machine according to claim 1, further comprising at least one sensor configured to detect at least one of an open position and the closed position of at least one of the housing door and the installation door, wherein the at least one sensor is a mechanically operable position button or switch.

5. The dialysis machine according to claim 1, wherein the housing door has an inside surface and an outside surface and wherein the installation space is arranged approximately flush with the housing door on the inside surface and the outside surface.

6. The dialysis machine according to claim 1, wherein the installation door is configured such that, in the closed position, the installation door is approximately flush with the housing door on the outside.

7. The dialysis machine according to claim 1, further comprising a collection device in the installation space for collecting a leakage volume of a fluid leaking from the device component in the installation space.

8. The dialysis machine according to claim 7, wherein the collection device has a bottom area that confines at least a portion of the installation space.

9. The dialysis machine according to claim 1, wherein the at least one wall is a wall on the rear of the housing.

10. The dialysis machine of claim 1, wherein the installation space further comprises a bicarbonate cartridge and/or a blood pressure cuff.

11. The dialysis machine according to claim 1, wherein the installation space has at least one of a retainer or an interface for the at least one device component contained in the installation space.

* * * * *